United States Patent [19]

Buzby, Jr. et al.

[11] Patent Number: 4,721,809
[45] Date of Patent: Jan. 26, 1988

[54] ALKYLSULFONAMIDO OR PERFLUOROALKYLSULFONAMIDO BENZENESULFONAMIDES

[75] Inventors: George C. Buzby, Jr., Blue Bell; Thomas J. Colatsky, Paoli, both of Pa.

[73] Assignee: American Home Products Corporation, New York, N.Y.

[21] Appl. No.: 909,133

[22] Filed: Sep. 18, 1986

[51] Int. Cl.$^4$ .................................... C07C 143/72
[52] U.S. Cl. ................................................ 564/82
[58] Field of Search .................................. 564/82

[56] References Cited

U.S. PATENT DOCUMENTS

| | | | |
|---|---|---|---|
| 2,233,296 | 2/1941 | Nelles et al. | 564/89 |
| 3,580,949 | 5/1971 | Gruenman et al. | 564/86 |
| 4,564,386 | 1/1986 | Konishi et al. | 564/82 |

FOREIGN PATENT DOCUMENTS

| | | |
|---|---|---|
| 1912848 | 10/1969 | Fed. Rep. of Germany . |
| 7237413 | 9/1972 | Japan . |
| 1053204 | 12/1966 | United Kingdom . |

OTHER PUBLICATIONS

Wohl et al., Abstracts of Papers, 192nd ACS National Meeting, Sep. 7-12, 1986.
Silberg et al., ACAD Rep Populace Romire, Fillala Clug, Studee Cercetari Med., 10 241-252 (1959).
Bexton et al., Pharmac. Ther. 17, 315-55 (1982).
Vaughan-Williams, J. Clin. Pharmacol. 24, 129-47 (1984).
Thomis et al., Ann. Rep. Med. Chem. 18, 99-108 (1983).

Primary Examiner—Anton H. Sutto
Attorney, Agent, or Firm—Richard K. Jackson

[57] ABSTRACT

This invention provides Class III anti-arrhythmic agents of the formula:

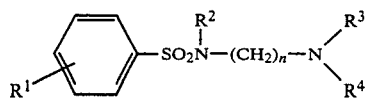

in which $R^1$ is alkylsulfonamido, arylsulfonamido, perfluoroalkylsulfonamido, $R^2$ and $R^3$ are hydrogen or alkyl, $R^4$ is alkyl, and n is 2 to 4, or a pharmaceutically acceptable salt thereof.

10 Claims, No Drawings

ALKYLSULFONAMIDO OR PERFLUOROALKYLSULFONAMIDO BENZENESULFONAMIDES

BACKGROUND OF THE INVENTION

Class III anti-arrhythmic agents may be categorized as having the ability to markedly prolong dog Purkinje fiber action potential duration without producing significant changes in maximal upstroke velocity. Unlike Class I anti-arrhythmic agents, a pure Class III agent displays no effects on cardiac sodium channels. The electrophysiologic properties of a compound defining a Class III activity profile are observed in vivo as negligible effects on atrial, ventricular and H-V conduction lines while producing a marked increase (greater than 20 percent) in both the atrial and ventricular refractory period. In contrast, Class I agents will demonstrate a marked slowing of ventricular conduction velocity, generally without significant changes in the refractory period. Recent reviews of these agents are by Bexton et al., Pharmac. Ther. 17, 315–55 (1982); Vaughan-Williams, J. Clin. Pharmacol. 24, 129–47 (1984) and Thomis et al., Ann. Rep. Med. Chem. 18, 99–108 (1983).

German Offenlegungsschrift 1912848 discloses in Example 5 the intermediate $N^1$-(2-isopropylaminoethyl)-$N^4$-acetyl-sulfanilamide which is used to produce 1-sulfanilyl-2-imino-3-isopropyl-imidazolidin said to be useful as a hypoglycemic agent.

Silberg et al., ACAD Rep. Populace Romire, Fillala Clug, Studee Cercetari Med., 10 244–52 (1959) discloses p-acetylamino-N-(2-diethylaminoethyl)benzenesulfonamide among other compounds compared in their anti-arrhythmic properties with procainamide.

The Abstracts of Papers to be presented at the 192nd ACS National Meeting, Sept. 7–12, 1986 at Anaheim, Calif. reports Abstract 9 by R. A. Wohl et al. which discloses N-[2-(diethylamino)ethyl]-4-[(methylsulfonyl)amino]benzamide hydrochloride projected as a potential Class III anti-arrhythmic agent.

DESCRIPTION OF THE INVENTION

In accordance with this invention there is provided a group of anti-arrhythmic agents classified by their pharmacological profile as Class III anti-arrhythmic agents of the formula:

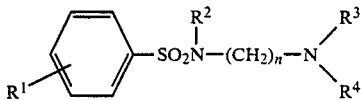

in which
R$^1$ is alkylsulfonamido of 1 to 6 carbon atoms, arylsulfonamido of 6 to 10 carbon atoms, perfluoroalkylsulfonamido of 1 to 6 carbon atoms,
R$^2$ is hydrogen or alkyl of 1 to 6 carbon atoms;
R$^3$ is hydrogen or alkyl of 1 to 6 carbon atoms;
R$^4$ is alkyl of 1 to 6 carbon atoms; and
n is one of the integers 2, 3 or 4;
or a pharmaceutically acceptable salt thereof.

Preferred compounds of the group described above are those in which R$^1$ is CH$_3$SO$_2$NH—, C$_6$H$_5$SO$_2$NH— or CF$_3$SO$_2$NH—. The most preferred compounds are embraced by the structural formula:

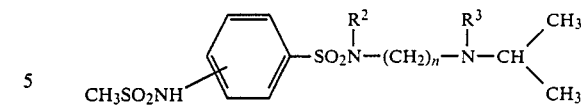

where
R$^2$ is hydrogen or straight or branched chain alkyl of 1 to 6 carbon atoms;
R$^3$ is hydrogen or isopropyl; and
n is one of the integers 2, 3 or 4;
or a pharmaceutically acceptable salt thereof.

The pharmaceutically acceptable salts of the anti-arrhythmic agents of this invention are prepared directly by neutralization of the free base. These physiologically acceptable salts may be formed with organic or inorganic acids such as hydrochloric, hydrobromic, phosphoric, sulfuric, sulfamic, nitric, methylsulfonic, acetic, maleic, succinic, fumaric, tartaric, citric, salicylic, lactic, naphthalenesulfonic acid, and the like.

The compounds of this invention may be prepared by reaction of an appropriately substituted benzene sulfonyl halide with an appropriately substituted α,ω-alkane diamine of 2 to 4 carbon atoms. These reactants are generally known compounds and otherwise are routinely prepared by techniques well within the skill of the chemist. The compounds may also be prepared by acylation of a free amino group on the benzene ring of the desired sulfonamide in the absence of an ω-nitrogen proton, as will trifluoromethylsulfonylanhydride and the like, in the presence of an acid binding agent such as triethylamine.

The compounds of this invention demonstrate anti-arrhythmic activity when tested in the standard experimental animal in accordance with the following procedure:

Miniature pigs of either sex weighing 11–24 kg were anesthetized by administration of 35 mg/kg sodium pentobarbital i.p. and ventilated with room air following tracheotomy using a Harvard respirator pump set to deliver 20 ml/kg at a rate of 20/min. The left femoral artery and vein were cannulated for the recording of blood pressure and for drug administration, respectively. Blood pressure and lead II EKG were recorded on a Beckman RM dynograph recorder (Model R-612).

The heart was exposed by a left thoracotomy performed at the fifth intercostal space. A silk ligature was placed beneath the left anterior descending coronary artery (LAD) about 1 cm from its origin and distal to the septal artery branch. The artery was occluded by lifting the vessel with the ligature and quickly placing a bull-dog clamp (3×12 mm pudded jaws) over the artery. The clamp remained in place for a period of 20 min. Removal of the clamp produced a rapid reperfusion of the ischemic myocardium as evidenced by the return of normal color to the myocardium distal to the site of occlusion. Ectopic activity was monitored during occlusion and reperfusion by recording the lead II EKG at chart speeds of 5–25 mm/s. Animals were allowed to stabilize for at least 30 min prior to drug administration.

Pigs were randomized into groups receiving either vehicle or test drug at 5 mg/kg i.v. Animals surviving the period of occlusion were subsequently reperfused. No attempt was made to resuscitate animals experiencing ventricular fibrillation (VF) at any time following occlusion. Efficacy was established by noting the rate of survival of treatment vs. control groups using Fisher's exact test or Mantel-Haenszel test for the survival curves. In the absence of treatment, less than 30 percent of the animals survive the period of occlusion, with a mean time to death onset of 8-12 min. An effective compound either prevented death or prolonged survival time.

The compounds of this invention display a Class III anti-arrhythmic profile. Of these, the products of Examples 1 and 4 are representative. The Class III antiarrhythmic activity was established in accordance with the following standard test procedure:

Bundles of free-running Purkinje fibers with attached myocardium obtained from either ventricle of adult dog heart were pinned without stretching to the bottom of a 10 ml tissue chamber and continuously superfused with oxygenated Tyrode's solution at a flow rate of 10 ml/min. The composition of the Tyrode's solution was (mM): NaCl 150; KCl 4.0; $CaCl_2$ 2.7; $MgCl_2$ 0.5; HEPE buffer (7.4) 10; dextrose 5.5. The solution was aerated with 100% $O_2$. Bath temperature was maintained at 36±0.5° C. by circulating the superfusate through a thermostatically controlled water bath immediately prior to entering the tissue chamber.

The preparations were stimulated through bipolar Teflon-coated platinum wires, bared at the tips, placed on the endocardial surface of the attached myocardium, using a W.P.I. digital stimulator set to deliver constant current pulses 1-2 msec in duration at cycle lengths (c.l.) of 330 or 1000 msec. Stimulus strength was set at approximately 2× diastolic threshold, and adjusted as required throughout the experiment. All preparations were allowed to equilibrate in the tissue chamber for at least 1 hour before measurements were begun. Subsequently, a minimum of 60 minutes was allowed for equilibration with each drug-containing superfusate before post-drug measurements were made. Impalements were made at 6-10 sites throughout the preparation before and after drug exposure. Offset potentials were re-checked at the conclusion of each experiment.

Glass microelectrodes filled with 3M KCl were coupled to high impedance negative capacitance electrometers (W.P. Instruments, New Haven, CT), and Ag-/AgCl half-cells used as reference electrodes. The first derivative of the action potential upstroke (Vmax) was obtained using an analog differentiator circuit, coupled to a peak-hold circuit that retained the recorded value of Vmax for 30-70 msec. Action potential and Vmax tracings were displayed on a Tektronix storage oscilloscope, and photographed for later analysis. In addition, chart paper recordings of Vmax were obtained using the peak-hold device output.

Fresh stock solutions of drug were prepared for each experiment. Compounds were dissolved in distilled water at total concentrations of 1-10 mg/ml, and subsequently diluted to a final concentration of 3 $\mu$M in appropriate volumes of normal Tyrode's solution for evaluation.

Action potential (AP) parameters measured included: diastolic take-off potential (or activation voltage, $V_{act}$); AP overshoot ($V_{os}$); AP duration measured as the time taken to repolarize to −20 mV ($APD_{20}$), −60 mV ($APD_{60}$), and −80 mV ($APD_{80}$); and maximal upstroke velocity (Vmax). Data were compared using a two-sample t-test, with statistical significance taken as $p<0.05$. An increase in $APD_{60}$ that occurred without a significant change in Vmax was taken, by definition, to indicate Class III anti-arrhythmic activity.

Based upon the activity profile elicited by the compounds of this invention in the above-described standard scientifically recognized test models, the compounds are established as anti-arrhythmic agents useful in the treatment of cardiac arrhythmias and conditions characterized by coronary arteries vasospasm. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from about 1 to about 5 milligrams per kilogram host body weight (preferably from 2 to 10 mg/kg) i.v., and from about 2 to about 10 mg/kg (preferably 5 to 20 mg/kg) p.o., to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 50 milligrams to about 400 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the change in action potential duration and upstroke velocity, the time to death and percent survival, where tested, are provided.

EXAMPLE 1

4-methylsulfonamido-N-[2-[bis(1-methylethyl)amino]ethyl]-N-(1-methylethyl)benzene sulfonamide 4-methylsulfonamidobenzenesulfonyl chloride (16.45 g, 0.061 moles) was added portionwise as a solid over one hour to a solution of N,N,$N^1$-tri-isopropylethylenediamine (11.36 g, 0.061 moles) and triethylamine (6.16 g, 0.061 moles) in methylene chloride (300 ml). After addition, the reaction was stirred one hour, washed with $NaHCO_3$ solution then brine and the solvent was removed. The gummy residue was chromatographed on dry column silica gel (400 g) using 10% MeOH/EtOAc to give the pure product free base (10.1 g). Treatment of the free base with isopropanolic HCl gave the monohydrochloride salt as a white solid, (11.92 g)-m.r. 209°-211° C.

Analysis for: $C_{18}H_{34}ClO_4N_3S_2$: Calculated: C, 47.41; H, 7.51; N, 9.21. Found: C, 47.16; H, 7.29; N, 8.83.

3 $\mu$M, 1000 msec c.l.: %$\Delta APD_{60}=35$; %$\Delta Vmax=8$. Time to death: 18.3 min; 67% survival.

EXAMPLE 2

4-methylsulfonamido-N-[2-[bis(1-methylethyl)amino]ethyl]benzene sulfonamide 4-methylsulfonamidobenzenesulfonyl chloride (2.70 g) was added portionwise to N,N-di-isopropyl ethylene diamine (1.44 g) and triethylamine (1.0 g) in methylene chloride (250 ml). After stirring for one hour, washing with water and removal of solvent there was obtained a yellow gum (3.4 g). Chromatography on silica gel with 10% MeOH/EtOAc gave the pure product (2.67 g). The corresponding hydrochloride salt was obtained by treatment with isopropanol/HCl—2.41 g, m.r. 202°–204° C.

Analysis for: $C_{15}H_{27}O_4N_3S_2HCl$: Calculated: C, 43.52; H, 6.82; N, 10.15. Found: C, 43.89; H, 6.86; N, 9.86.

3 μM, 1000 msec c.l.: %ΔAPD$_{60}$=14; %ΔVmax=−22.

EXAMPLE 3

4-methylsulfonamido-N-[2-[(1-methylethyl)amino]ethyl]benzene sulfonamide 4-methylsulfonamidobenzenesulfonyl chloride (2.70 g) was added portionwise to a 0.01 mole portion of N-isopropylethylenediamine and triethylamine (0.01 mole) in methylene chloride (250 ml) to obtain a white solid which precipitated from the methylene chloride reaction mixture 2.62 g, m.r. 180°–182° C. This solid was washed well with methylene chloride, dissolved in isopropanol/HCl/methanol and the methanol boiled away. The product was precipitated and filtered to yield 1.65 g, m.r. 158°–160° C.(d).

Analysis for: $C_{12}H_{21}N_3O_4S_2 \cdot HCl$: Calculated: C, 38.76; H, 5.69; N, 11.30. Found: C, 38.77; H, 5.92; N, 11.17.

3 μM, 1000 msec c.l.: %ΔAPD$_{60}$=6; %ΔVmax=−8.

EXAMPLE 4

4-methylsulfonamido-N-(1-methylethyl)-N-[2-[(1methylethyl)amino]ethyl]benzenesulfonamide 4-methylsulfonamidobenzenesulfonyl chloride (2.70 g, 0.01 m) was added as a solid (portionwise as before) to N,N$^1$-di-isopropylethylene diamine (2.88 g, 0.02 m) and the reaction worked up. Removal of solvent yielded the solid product 1.94 g, m.r. 190°–195° C. which was washed well with methylene chloride. Treatment with isopropanol/HCl gave the title compound 1.47 g, m.r.—220°–222° C.

Analysis for: $C_{15}H_{27}O_4N_3S_2HCl$: Calculated: C, 43.52; H, 6.82; N, 10.15. Found: C, 43.76; H, 6.76; N, 10.01.

3 μM, 1000 msec c.l.: %ΔAPD$_{60}$=31; %ΔVmax=12.

Time to death: 18 min; 44% survival.

EXAMPLE 5

N-[3-[(1-methylethyl)amino]propyl]-4-methane sulfonamido benzene sulfonamide p-Methanesulfonamidobenzenesulfonyl chloride (2.16 g, 0.008 m) was added portionwise as a solid to N-isopropyl propane 1,3 diamine (0.93 g) and triethylamine (0.081 g) in $CH_2Cl_2$ (50 ml) with vigorous stirring. After 1.5 hours a gum was precipitated. The $CH_2Cl_2$ was decanted and the residue stirred with a further 50 ml of methylene chloride which was again decanted and the procedure continued with diethyl ether (50 ml) overnight. The residue was dissolved in isopropyl alcohol/HCl minimum amount and chilled to provide the product (1.02 g) m.r. 100°–105° C. as a hydrochloride hemihydrate with a trace of isopropanol.

Analysis for: $C_{13}H_{24}ClO_4N_3S_2 \cdot \frac{1}{2}H_2O$: Calculated: C, 39.54; H, 6.38; N, 10.64. Found: C, 39.72; H, 6.43; N, 10.76.

3 μM, 1000 msec c.l.: %ΔAPD$_{60}$=16; %ΔVmax=0.

EXAMPLE 6

N-[2-[bis(1-methylethyl)amino]ethyl]-N-(1-methylethyl)-4-[(trifluoromethylsulfonyl)amino]benzenesulfonamide p-Nitrobenzenesulfonyl chloride was reacted with N,N',N'-triisopropyl ethylene diamine to obtain the free base of N-[2-[bis(1-methylethyl)amino]ethyl]-N-(1-methylethyl)-4-nitrobenzene sulfonamide as a yellow solid, m.r. 98°–100° C.

Analysis for: $C_{17}H_{29}N_3O_4S$: Calculated: C, 54.96; H, 7.87; N, 11.31. Found : C, 54.43; H, 7.67; N, 11.66.

The product of the preceding paragraph was reduced catalytically in the system $Pt/H_2$/tetrahydrofuran. Isolated from the product mixture was 4-amino-N-[2-[bis(1-methylethyl)amino]ethyl]-N-(1-methylethyl)benzenesulfonamide, which was crystallized from isopropanol, m.r. 100°–102° C.

Analysis for: $C_{17}H_{31}N_3O_2S$: Calculated: C, 59.79; H, 9.15; N, 12.30. Found: C, 59.54; H, 9.16; N, 12.22.

4-amino-N-[2-[bis(1-methylethyl)amino]ethyl]-N-(1-methylethyl)-benzenesulfonamide (2.0 g, 0.0058 m) in $CH_2Cl_2$ (50 ml) containing triethylamine (0.60 g, 0.0058 m) at 0° C. was treated with trifluoromethane sulfonic anhydride (0.976 ml, 0.0058 m) dropwise over one half hour. The solution was worked with aqueous sodium bicarbonate, then brine and stripped to give the crude product as a gum. Solution in 20 percent methanol/ethyl acetate produced the solid free base (1.87 g, m.r. 210°–213° C.(d).

Analysis for: $C_{18}H_{30}F_3O_4N_3S_2$: Calculated: C, 45.65; H, 6.39; N, 8.89. Found: C, 45.16; H, 6.29; N, 8.39.

Treatment of this product with isopropanol/HCl gave the hydrochloride salt (1.38 g, m.r. 213°–215° C.).

Analysis for: $C_{18}H_{30}F_3O_4N_3S_2 \cdot HCl$: Calculated: C, 42.39; H, 6.13; N, 8.24. Found: C, 42.48; H, 6.14; N, 7.99.

EXAMPLE 7

N-[2-[bis(1-methylethyl)amino]ethyl]-4-[(trifluoromethylsulfonyl)amino]benzene sulfonamide p-Nitrobenzenesulfonyl chloride was reacted with N,N-diisopropyl ethylene diamine to give N-[2-[bis(1-methylethyl)amino]ethyl]-4-nitrobenzene sulfonamide as the free base, m.r. 86°–88° C.

Analysis for: $C_{14}H_{23}N_3O_4S$: Calculated: C, 51.05; H, 7.04; N, 12.76. Found: C, 51.34; H, 7.15; N, 12.66.

The product of the preceding paragraph was catalytically reduced in methanol/$PtO_2$ to provide 4-amino-N-[2-[bis(1-methylethyl)amino]ethyl]benzenesulfonamide, m.r. 115°–117° C.

Analysis for: $C_{14}H_{25}N_3O_2S$: Calculated: C, 56.16; H, 8.42; N, 14.03. Found: C, 56.23; H, 8.46; N, 14.10.

4-amino-N-[2-[bis(1-methylethyl)amino]ethyl]benzenesulfonamide (4.0 g, 0.0134 m) in methylene chloride (50 ml) containing triethylamine (1.35 g, 0.0134 m) at 0° C. was treated by dropwise addition, with vigorous stirring, of trifluoromethane sulfonic anhydride (3.77 g, 2.25 ml, 0.0134 m) over one hour. The solution was washed with aqueous $Na_2CO_3$ then brine and stripped. The resulting crude gum (about 6.0 g) was dissolved in 20% MeOH/EtOAc to provide the product free base as a white solid (2.25 g, m.r. 225°–227° C.

Analysis for: $C_{15}H_{24}O_4N_3S_2$: Calculated: C, 41.75; H, 5.61; N, 9.74. Found: C, 41.84; H, 5.56; N, 9.64.

Conversion to the hydrochloride was made with isopropanol/HCl, recrystallized from methanol/isopropanol as beautiful flakes (2.11 g, m.r. 238°–240° C.).

Analysis for: $C_{15}H_{24}F_3O_4N_3S_2 \cdot HCl$: Calculated: C, 38.50; H, 5.38; N, 8.98. Found: C, 38.72; H, 5.43; N, 8.90.

What is claimed is:

1. A compound of the formula:

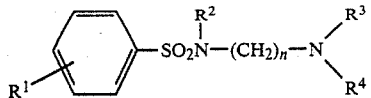

in which
 $R^1$ is alkylsulfonamido of 1 to 6 carbon atoms or perfluoroalkylsulfonamido of 1 to 6 carbon atoms;
 $R^2$ is hydrogen or alkyl of 1 to 6 carbon atoms;
 $R^3$ is hydrogen or alkyl of 1 to 6 carbon atoms;
 $R^4$ is alkyl of 1 to 6 carbon atoms; and
 n is one of the integers 2, 3 or 4;
or a pharmaceutically acceptable salt thereof.

2. A compound of the formula:

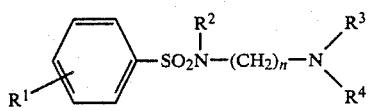

in which
 $R^1$ is $CH_3SO_2NH-$ or $CF_3SO_2NH-$;
 $R^2$ is hydrogen or alkyl of 1 to 6 carbon atoms;
 $R^3$ is hydrogen or alkyl of 1 to 6 carbon atoms;
 $R^4$ is alkyl of 1 to 6 carbon atoms; and
 n is one of the integers 2, 3 or 4;
or a pharmaceutically acceptable salt thereof.

3. A compound of the formula:

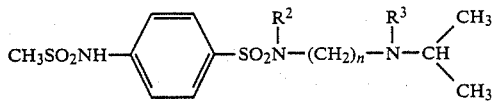

in which
 $R^2$ is hydrogen or isopropyl;
 $R^3$ is hydrogen or isopropyl; and
 n is one of the integers 2 or 3;
or a pharmaceutically acceptable salt thereof.

4. The compound of claim 3 which is 4-methylsulfonamido-N-[2-[bis(1-methylethyl)amino]ethyl]-N-(1-methylethyl)benzene sulfonamide or a pharmaceutically acceptable salt thereof.

5. The compound of claim 3 which is 4-methylsulfonamido-N-[2-[bis(1-methylethyl)amino]ethyl]benzene sulfonamide or a pharmaceutically acceptable salt thereof.

6. The compound of claim 3 which is 4-methylsulfonamido-N-[2-[(1-methylethyl)amino]ethyl]benzenesulfonamide or a pharmaceutically acceptable salt thereof.

7. The compound of claim 3 which is 4-methylsulfonamido-N-(1-methylethyl)-N-[2-[(1-methylethyl)amino]ethyl]benzenesulfonamide or a pharmaceutically acceptable salt thereof.

8. The compound of claim 3 which is N-[3-[(1-methylethyl)amino]propyl]-4-methane sulfonamido benzenesulfonamide or a pharmaceutically acceptable salt thereof.

9. The compound of claim 2 which is N-[2-[bis(1-methylethyl)amino]-ethyl]-N-(methylethyl)-4-[(trifluoromethylsulfonyl)amino]benzenesulfonamide or a pharmaceutically acceptable salt thereof.

10. The compound of claim 2 which is N-[2-[bis(1methylethyl)amino]-ethyl]-4-[(trifluoromethylsulfonyl)amino]benzenesulfonamide or a pharmaceutically acceptable salt thereof.

* * * * *

REEXAMINATION CERTIFICATE (1076th)
United States Patent
Buzby, Jr. et al.

[11] B1 4,721,809
[45] Certificate Issued Jun. 6, 1989

[54] ALKYLSULFONAMIDO OR PERFLUOROALKYLSULFONAMIDO BENZENESULFONAMIDES

[75] Inventors: George C. Buzby, Jr., Blue Bell; Thomas J. Colatsky, Paoli, both of Pa.

[73] Assignee: American Home Products Corporation, New York, N.Y.

Reexamination Request:
No. 90/001,618, Sep. 30, 1988

Reexamination Certificate for:
Patent No.: 4,721,809
Issued: Jan. 26, 1988
Appl. No.: 909,133
Filed: Sep. 18, 1986

[51] Int. Cl.$^4$ .................... C07C 143/72
[52] U.S. Cl. ............................. 564/82
[58] Field of Search ....................... 558/82

[56] References Cited

U.S. PATENT DOCUMENTS

4,544,654  10/1985  Davey et al. ............ 558/83
4,629,739  12/1986  Davey et al. ............ 558/83

FOREIGN PATENT DOCUMENTS

0158775  10/1985  European Pat. Off.

OTHER PUBLICATIONS

Lumma et al, "Journal of Medicinal Chemistry", vol. 30, No. 5, (1987), pp. 755–758.

Primary Examiner—Anton H. Sutto

[57] ABSTRACT

This invention provides Class III anti-arrhythmic agents of the formula:

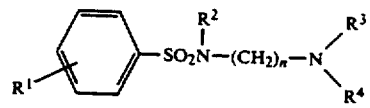

in which $R^1$ is alkylsulfonamido, arylsulfonamido, perfluoroalkylsulfonamido, $R^2$ and $R^3$ are hydrogen or alkyl, $R^4$ is alkyl, and n is 2 to 4, or a pharmaceutically acceptable salt thereof.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4–6 and 8–10 are cancelled.

Claim 3 is determined to be patentable as amended.

Claim 7, dependent on an amended claim, is determined to be patentable.

3. A compound of the formula:

in which
 $R^2$ is [hydrogen or] isopropyl;
 $R^3$ is hydrogen [or isopropyl]; and
 n is one of the integers 2 or 3;
or a pharmaceutically acceptable salt thereof.